United States Patent [19]
Wenzhi

[11] Patent Number: 5,500,374
[45] Date of Patent: Mar. 19, 1996

[54] METHOD FOR DIAGNOSING DIABETES MELLITUS AND DEVICE THEREFOR

[75] Inventor: Hu Wenzhi, Nagoya, Japan

[73] Assignee: Soichi Inoue, Nagoya, Japan

[21] Appl. No.: 107,122

[22] Filed: Aug. 17, 1993

[30] Foreign Application Priority Data

Oct. 5, 1992 [JP] Japan ................................ 4-290740

[51] Int. Cl.$^6$ ................................................. G01N 30/02
[52] U.S. Cl. .................... 436/161; 73/61.53; 210/198.2; 210/656; 210/660; 436/173
[58] Field of Search ................................ 436/161, 173, 436/63; 422/70; 73/61.52, 61.53, 61.55; 210/656, 660, 198.2

[56] References Cited

U.S. PATENT DOCUMENTS

| | | | |
|---|---|---|---|
| 4,168,147 | 9/1979 | Acuff | 436/161 X |
| 4,735,777 | 4/1988 | Mitsui et al. | 422/70 |
| 4,895,808 | 1/1990 | Romer | 436/178 |
| 4,992,531 | 2/1991 | Patroni et al. | 530/351 |
| 5,032,503 | 7/1991 | Khanna et al. | 435/7.6 |
| 5,055,398 | 10/1991 | Fujie et al. | 436/174 X |
| 5,139,023 | 8/1992 | Stanley et al. | 128/637 |
| 5,231,031 | 7/1993 | Szwergold et al. | 436/173 X |
| 5,245,008 | 9/1993 | Dickhardt et al. | 530/305 |

OTHER PUBLICATIONS

Bennington et al. Saunders Dictionary & Encylopedia of Laboratory Medicine and Technology, W B Saunders Company 1984 pp. 436–437.
Mandrup, Journal of Chromatography, vol. 604, pp. 267–281, 1992.
Zlatkis et al. Clinical Chemistry, vol. 27/6, pp. 789–797, 1981.
Nomura et al. Analytical Chemistry, vol. 60, pp. 2509–2512, 1988.
Tramposch et al. Journal of Chromatography, vol. 544, pp. 113–123, 1990.
Kurganov et al. Journal of Chromatography, vol. 548, pp. 207–214, 1991.
HU et al. Bulletin Chemical Society of Japan, vol. 66, No. 5, pp. 1420–1423, May 1993.
Lochner et al. Journal of Chromatography, vol. 378, pp. 267–282, 1986.
Hu et al. Analytical Chemistry, vol. 65, pp. 2204–2208, Sep. 1, 1993.
Lee et al. Journal of Chromatography, vol. 158, pp. 377–386, 1978.
"Liquid Chromatographic Separation and Indirect Detection of Inorganic Anions Using Iron (II) 1, 10–Phenanthroline as a Mobile Phase Additive", Rigas, et al., Anal. Chem. 58:2226–2233 (1986).
"Micelle Exclusion Chromatography of Inorganic Anions", Tetsuo Okada, Anal. Chem. 60:1511–1516 (1988).
"Isotachophoresis", J. L. Beckers et al., J. Chromatog., 51:339–342 (1970).

Primary Examiner—James C. Housel
Assistant Examiner—Jan M. Ludlow
Attorney, Agent, or Firm—Finnegan, Henderson, Farabow, Garrett & Dunner

[57] ABSTRACT

A rapid, simple and reliable method and device for diagnosing diabetes mellitus under no influence of diet. The method for diagnosing diabetes mellitus involves injecting a saliva sample from a patient suspected of having diabetes mellitus into a stationary phase in a separation column, thereafter eluting a phosphate buffer as an eluent to separate analytes contained in the saliva sample, subsequently detecting the individual separated analytes with a UV detector and electrostatic ion chromatography to produce a chromatogram, and then diagnosing diabetes mellitus based on the presence or absence of a chromato-peak of the diabetes mellitus-specific component. A zwitterionic stationary phase is employed as the stationary phase and contains a support carrier and a zwitterionic charged layer formed by coating a compound having an ammonium salt portion, a sulfonate ion portion or carboxylate ion portion on the surface of the support carrier.

1 Claim, 7 Drawing Sheets

R=H   NaTDC
R=OH  NaTC

METHOD FOR DIAGNOSING DIABETES MELLITUS AND DEVICE THEREFOR

BACKGROUND OF THE INVENTION

1. Field of the Invention

The present invention relates to a method for diagnosing diabetes mellitus and a device therefor. The present invention can be applied in various manners to clinical diagnosis and the like, requiring rapidness and accuracy.

2. Prior Art

As a method for diagnosing diabetes mellitus, the one to determine blood glucose level is generally known. As another such method, the one to determine 1,5-anhydro-D-glucitol in plasma is also illustrated.

3. Problems to be solved by the Invention

The method via blood glucose level has limitation to the application thereof, because blood glucose level of itself is unstable and readily depends on the diet, with limitation to the application thereof. The method has a problem in that a long period of time of testing is required.

The method to determine 1,5-anhydro-D-glucitol in plasma has problems in that the conditions for such determination are hard to control; the time required for sample preparation is long; and the deproteination is needed. At the test of a sample from a diabetic patient with a lowered 1,5-anhydro-D-glucitol level, the reliability on the measurement is low. That is, the level close to the lower limit of the 1,5-anhydro-D-glucitol range of non-diabetic patients (24.6±7.2 mg/liter) is proximate to the upper limit of the range of diabetic patients (7.3±7.2 mg/liter). Accordingly, the method is applied only in relation with other diagnostic tests, which is a limitation to the application thereof.

Ion chromatography having a stationary phase packed with an ion exchange resin is a known method for separating and analyzing a component (ion). As such ion chromatography, there have been known ion exchange method (Anal. Chem. 1975, 47, 1801–1809); ion exclusion method (Anal. Chem. 1989, 61, 1485–1489); ion interaction method (Anal. Chem. 1982, 54, 2601–2603; Anal. Chore. 1986, 58, 2226–2233); colloid particle exclusion method (Anal. Chem. 1988, 60, 1511–1516); electrophoresis (J. Chromatog. 51 (1970), 339–342) and a combination of reverse phase chromatography and ion exclusion method (Japanese Patent Laid-open No. 4-110657), and the like. However, it has not been known any method comprising these methods to diagnose the presence or absence of diabetes mellitus.

SUMMARY OF THE INVENTION

Object of the Invention

By overcoming the above drawbacks, the object of the present invention is to provide a rapid, simple and reliable method for diagnosing diabetes mellitus under no influence of diet, together with a device therefor.

Characteristics of the Invention

The present inventor has made various investigations as to whether or not diabetes mellitus can be diagnosed by a certain method, other than a method to analyze blood glucose level or a method to analyze plasma. Consequently, the inventor has found that a specific component exists in the saliva from a diabetic patient and that the separation and analysis thereof leads to the achievement of the present invention.

That is, the method for diagnosing diabetes mellitus in accordance with the present invention comprises injecting the saliva sample from a suspected case of diabetes mellitus into one end of a stationary phase packed in a separation column, thereafter eluting a phosphate buffer as an eluent to separate the analytes contained in the saliva sample, subsequently detecting the individual separated analytes with a UV detector to confirm that a predetermined chromatogram is demonstrated by electrostatic ion chromatography, the chromatogram developing a chromato-peak of the diabetes mellitus-specific component contained in the saliva of the patient, and establishing the diagnosis of diabetes mellitus on the basis of the presence of the peak, wherein a zwitterionic stationary phase is employed as the stationary phase, comprising a support carrier and a zwitterionic charged layer formed by directly or indirectly coating a compound having both positive and negative charges such as an ammonium salt portion, and a sulfonate ion portion or carboxylate ion portion on a molecule of the support carrier.

The device for diagnosing diabetes mellitus in accordance with the present invention comprises an eluent feeding pump, a separation column connected to the pump, a UV detector for detecting the analytes separated through the separation column, a recording device recording the results of the separation, and a saliva sample injector to inject the saliva sample from a suspected case of diabetes mellitus into a connecting tube connected in between the separation column and the pump, wherein the separation column is packed with a zwitterionic stationary phase comprising a support carrier and a zwitterionic charged layer formed by directly or indirectly coating a compound having an ammonium salt portion, and a sulfonate ion portion or carboxylate ion portion on the surface of the support carrier, characterized in that the recording device records the presence of the chromato-peak of the component specific to diabetes mellitus, if any, thereby establishing the diagnosis of diabetes mellitus.

Function

Ions are charged particles, so electrostatic repulsion and attract ion forces are induced between identically charged ions and between oppositely charged ions, respectively.

The electrostatic stationary phase to be used in the present ion separation and analysis method has a zwitterionic charged layer formed by coating a compound having both of positive-charge portion and a negative-charge portion on the surface of the support carrier. When analyte ions are then mobilized with an eluent (mobile phase) to pass through the electrostatic stationary phase, as shown in FIG. 2, the electrostatic repulsion and attraction forces simultaneously occur on the two charged portions of the electrostatic stationary phase. The combination of the electrostatic repulsion and attraction forces (total sum) consequently amounts to what is represented by Formula 1, depending on the number or intensity (degree) of the charges, the radius of hydrated ions and the like.

$$\Delta F = \sum_{i=1}^{n} \left( \epsilon_1 \frac{q(s)^+ q_A^n}{r_i^2} - \epsilon_2 \frac{q(s)^- q_A^n}{r_i^2} \right) \quad \text{[Formula 1]}$$

In formula 1, n represents the number of charges; $\epsilon_1$ and $\epsilon_2$ represent electrostatic conductivity; $q(s)^+$ and $q(s)^-$ represent the electron density of negative and positive charges of a stationary phase; $q_A$ represents the electron density of an analyte ion; and r and r' individually represent the electrostatically active distance. The combined electrostatic forces ($\Delta F$) function as another separation force for a separation column.

If $\Delta F<0$, electrostatic repulsion force is larger than electrostatic attraction force, and analyte ions cannot be stayed in the electrostatic column. On the contrary, analyte ions cannot be eluted from the column, if $\Delta F>\phi$ ($\phi$ represents the transfer force of the mobile phase). If $\Delta F$ satisfies the provision that $\phi \geq \Delta F \geq 0$, the analyte ions can be separated on the column. For example, if $\phi$ (water)$\geq \Delta F \geq 0$, the analyte ions can pass through the electrostatic column, even using purified water as an eluent. In the same fashion, if $\phi$ (eluent)$\geq \Delta F \geq 0$, the analyte ions can pass through the column, using the eluent.

The chromato-peak of the diabetes mellitus-specific component, contained in the saliva from diabetic patients, is demonstrated on the chromatogram, which presence establishes the diagnosis of diabetes mellitus.

Effect of the Invention

According to the method and device in accordance with the present invent ion, the chromato-peak of the component specific only to diabetes mellitus can be detected well, so that the diagnosis of diabetes mellitus can be established based on the presence of the specific peak, in rapid, simple and accurate manners with no influence of diet.

DETAILED DESCRIPTION OF THE INVENTION

In accordance with the present invention, a support carrier of any material, form or size may be used in the aforementioned "zwitterionic stationary phase", without any specific limitation, if a zwitterionic charged layer can be formed on the surface of the carrier. The material is illustrated, for example, by silica gel, polystyrene and the like, and the surface thereof is preferably porous for ready immobilization. Furthermore, the zwitterionic layer may directly be formed on a carrier to be used, through chemical reaction or physical adsorption; a zwitterionic charged layer may be formed on the surface of the carrier through a hydrophobic layer being formed thereon as an adhesive layer (in other words, indirectly formed on the surface of the carrier).

For example, a carrier comprises porous silica gel the aforementioned "zwitterionic stationary phase"; on the surface of the carrier is formed a hydrophobic layer obtained through alkylsilane reaction; and furthermore, the zwitterionic layer is adsorbed and formed onto the surface of the hydrophobic layer. The alkyl group of the alkylsilane is preferably the one with about 12 to 24 carbon atoms so as to provide hydrophobicity; the one with 18 carbon atoms is employed in general.

The aforementioned "compound having an ammonium salt portion (cation portion), and a sulfonate ion portion or carboxylate ion portion (anion portion)" may be illustrated by 3-[3-cholamidepropyl]dimethyl ammonio]-1-propanesulfonate or 3-[3-cholamidepropyl)dimethyl ammonio]-2-hydroxy-1-propanesulfonate or the like.

The term "eluent" (sometimes referred to as "mobile phase") means a phosphate buffer containing a phosphate salt and having a buffer action. As the buffer, a variety of known phosphate salts ($NaH_2PO_4$+ $Na_2HPO_4$, $NaH_2PO_4$+ citric acid, $NaH_2PO_4$+$NaHCO_3$, etc.) may generally be used with purified water and the like as a solvent, without limitation. Any solvent which can dissolve the phosphate salts can be used. Any ion concentration may be selected therefor.

As the "means" to detect the separated analytes, there may be used an ultraviolet (referred to as "IV" hereinafter) detector, because the analytes in the saliva samples from diabetic and non-diabetic patients (particularly, the specific component) have a UV absorption range of about 200 to 260 nm.

Embodiment

The present invent ion will now be explained in details with reference to examples.

(1) Electrostatic ion chromatography device and conditions therefor

Figure 1:
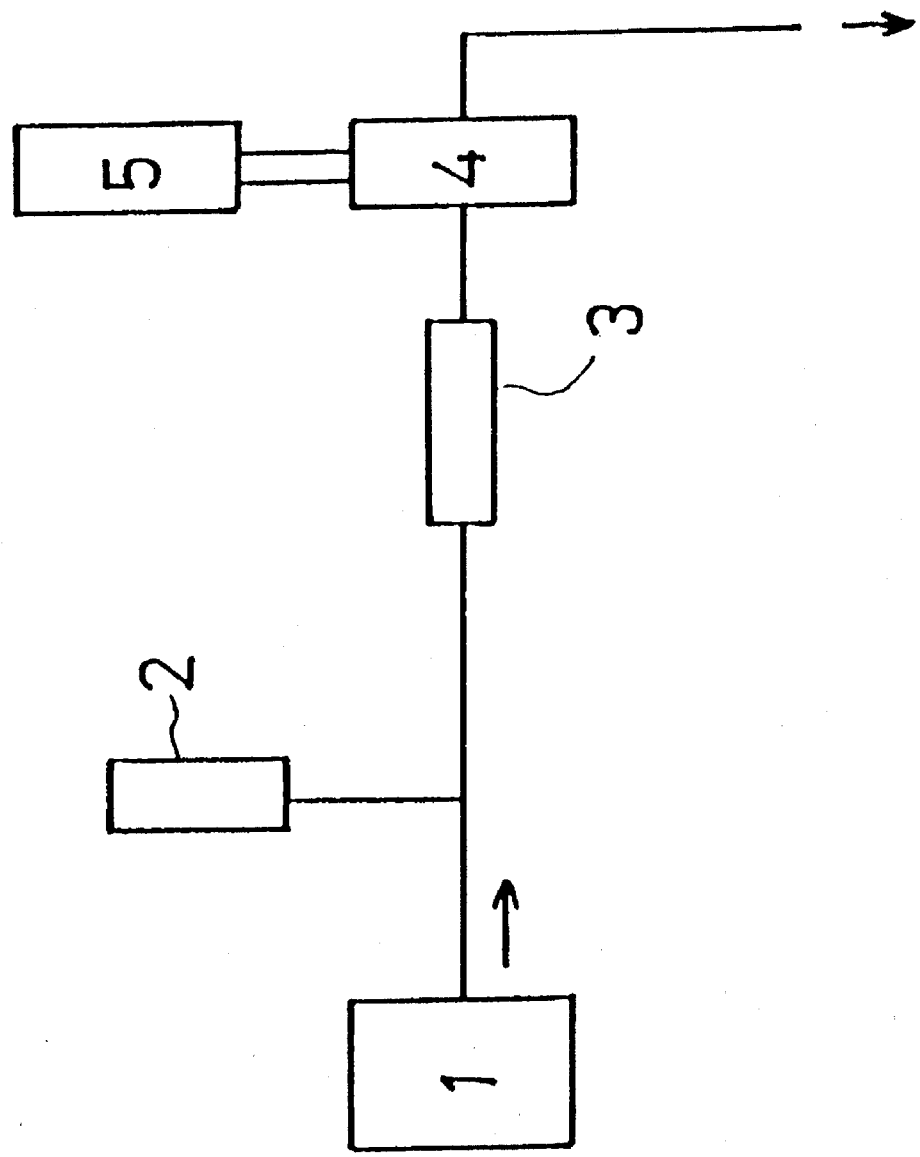
FIG. 1 is a schematic explanatory view of the device used in Example for diagnosing diabetes mellitus.

As shown in FIG. 1, the present device comprises an eluent feeding pump 1, a separation column 3 connected to the pump 1, a IV detector 4 for detecting the analytes separated through the separation column 3, a recording device 5 recording the results of the separation, and a liquid sample injector 2 to inject a saliva sample into a connecting tube connected in between the separation column 3 and the pump 1.

Figure 2:
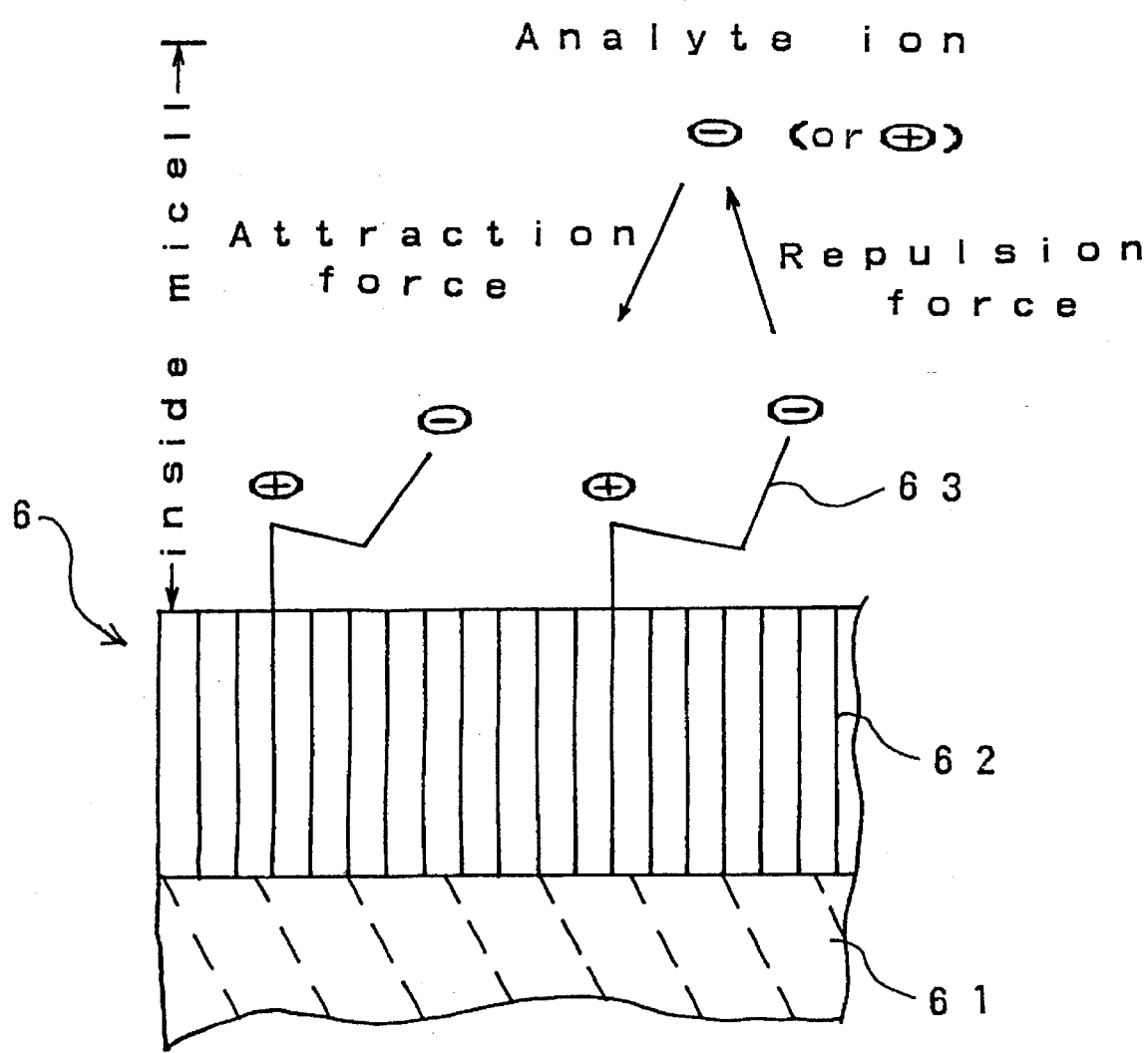
FIG. 2 is a schematic explanatory view of the state wherein the analytes pass through the zwitterionic stationary phase used in the Example.
Figure 3:
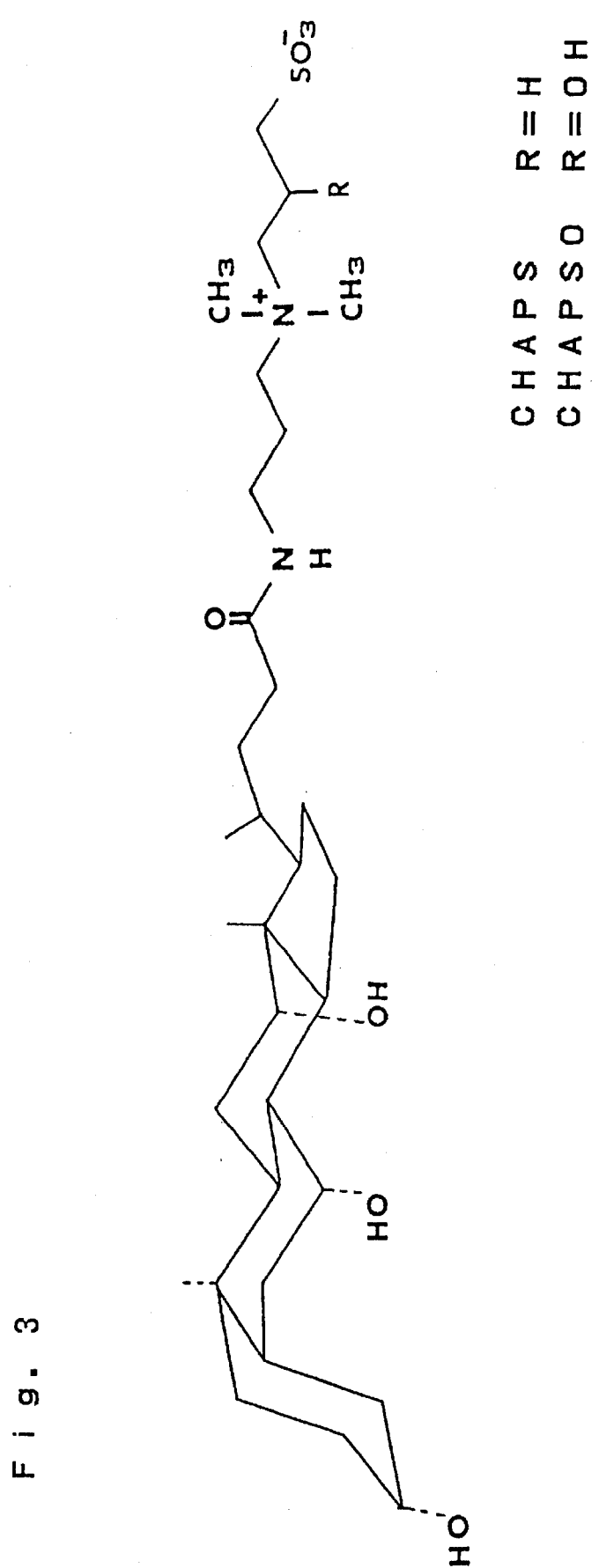
FIG. 3 is an explanatory view depicting the chemical structures of CHAPS and CHAPSO.
Figure 4:
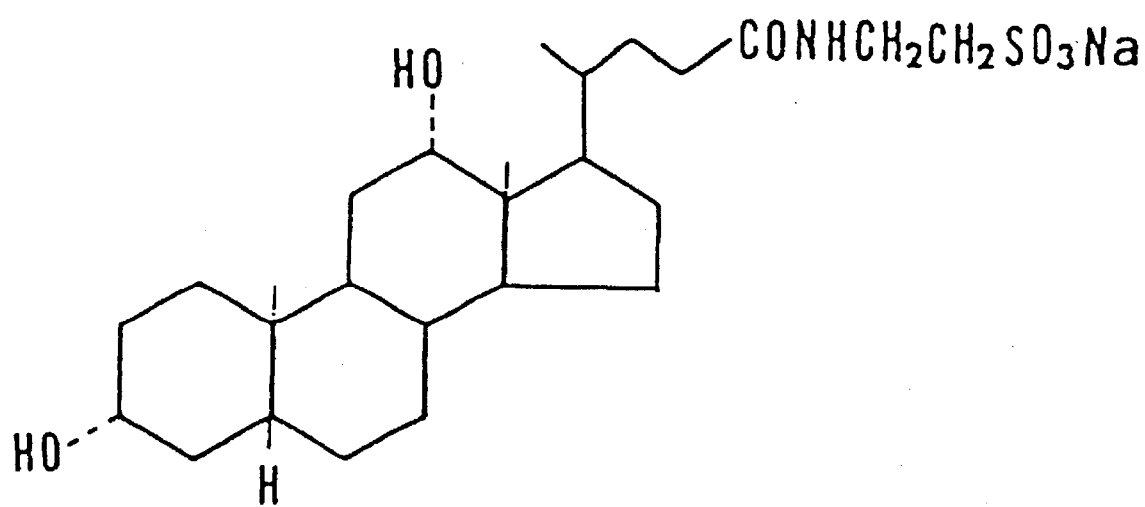
FIG. 4 is an explanatory view depicting the chemical structures of NaTDC and NaTC.

As such pump 1, "MF-2 Microfeeder" (manufactured by Azuma Electric Industry, Co. Ltd.) with a 0.5-ml gas-tight injector ("MS-GAN 050" as product name; manufactured by Ito Fuji Corporation) was used. As such sample injecting part 2, a microvalve ("ML-552" as product name; manufactured by JASCO CO. Ltd.; injection volume, 0.02 μl) was used. As such separation column 3, there was prepared firstly a column of 150 mm×0.35 mm in internal diameter, packed with 5- μm "Develosil ODS-5" (as product name; manufactured by Nomura Chemical; prepared by reacting porous silica gel with octadecyl silane; referred to as 13DS carrier). As shown in FIG. 2, subsequently, 3-[(3-Cholamidepropyl) dimethyl ammonio]-1-propanesulfonate (referred to as "CHAPS"; manufactured by Dojin Corporation, zwitterionic ion surfactant; depicted in FIG. 2) 63, was immobilized (coated) onto the surface of the ODS carrier (ODS layer, 62; the carrier thereof, 61) to prepare zwitterionic stationary phase 6.

The method for immobilization is as follows. An aqueous 30 mmol/liter micellar solution, as a predetermined surfactant passed through a microcolumn packed with the ODS carrier at a flow rate of 2.8 μl/min. for 20 minutes. Then, the column was washed with purified water at the same flow rate for 30 minutes. The concentration of the surfactant should be higher than the critical micelle concentration (CMC).

"UVIDEC-100V" (as product name; manufactured by JASCO) with a flow cell was used as UV detector (detection wave length of 215 to 230 nm) 4; "Chromatopack C-R4AX Data Processor" (as product name; manufactured by Shimadzu Seisakusho cCorporation) was used as a recording device 5. A aqueous buffer solution of phosphate salts ($NaH_2PO_4$: 10 mmol/liter+$Na_2HPO_4$: 10 mmol/liter ) as an eluent (mobile phase) was used, and this flow rate was 2.8 μl/min., the separation was done at room temperature.

(2) Diagnosis of diabetes mellitus

The following experiments were done with the above device under the above conditions.

A saliva sample from a diabetic or non-diabetic individual was collected through an injector. So as to remove the solid particles in the sample, the needle end of the injector was covered with cotton wool during the collection. Then, the cotton wool was removed prior to the injection of the saliva sample into the sample injecting part of a microvalve.

Figure 5:
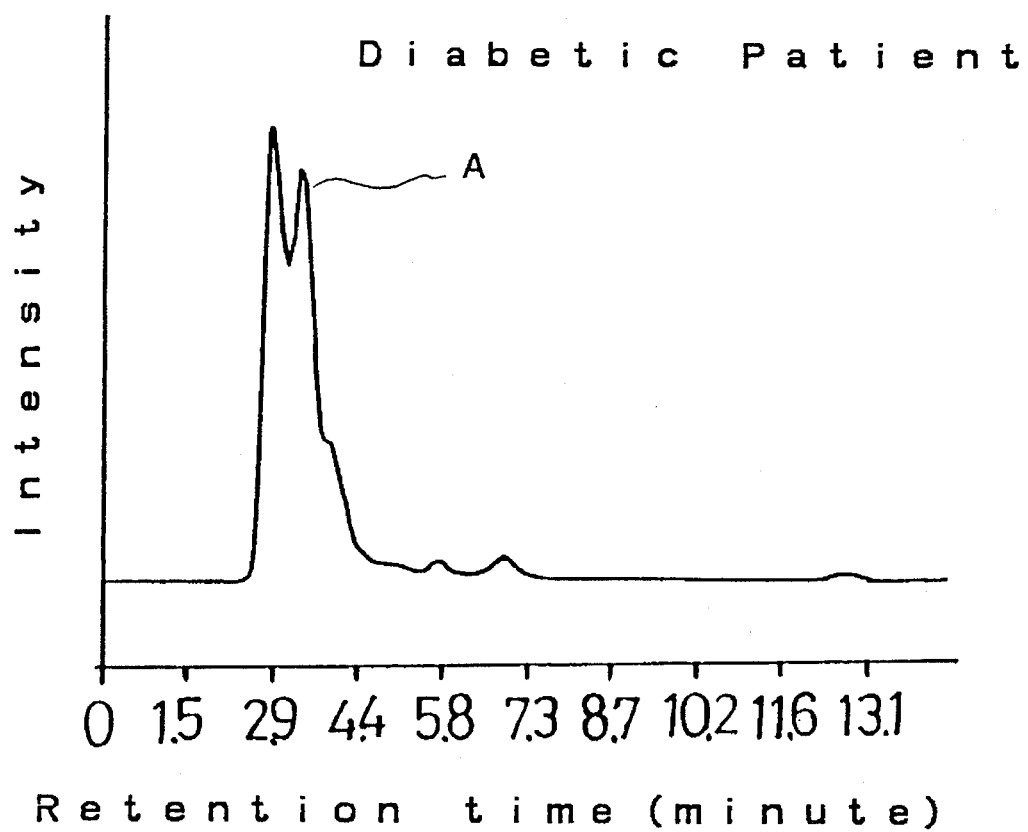
FIG. 5 is an explanatory view depicting the chromatogram from the analysis of the saliva sample from a diabetic patient in Example.
Figure 6:
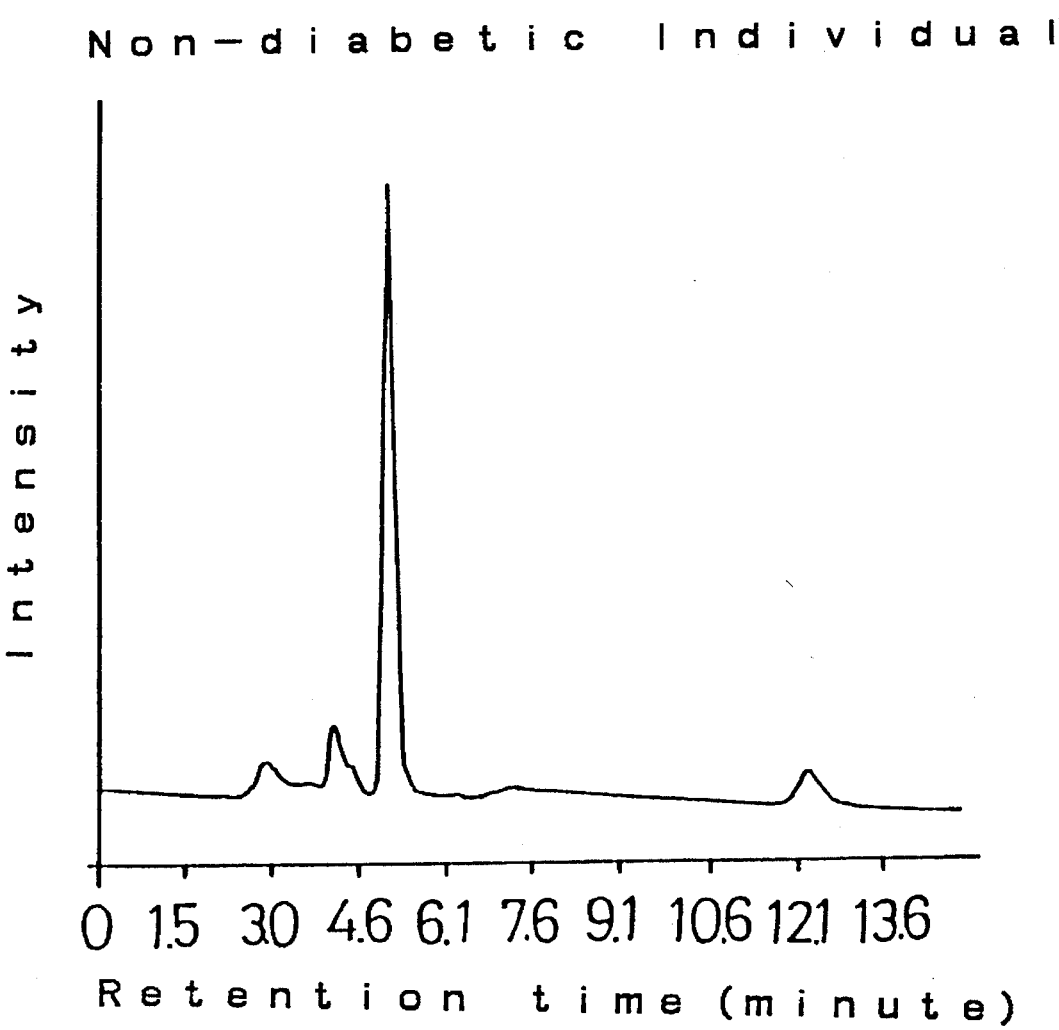
FIG. 6 is an explanatory view depicting the chromatogram from the analysis of the saliva sample from a non-diabetic individual in Example.

Analytical test was done about 50 cases of diabetes mellitus and 30 cases of non-diabetes mellitus. No diet control was imposed to the great number of the diabetic or non-diabetic patients; sample collection was done after diet, prior to diet or after the intake of drinks; and collection time had variation, such as in the morning or in the afternoon. For one example, the chromatogram of a certain diabetic patient among them, is shown in FIG. 5; that of a non-diabetic patient is shown in FIG. 6. The comparison thereof indicates that the chromato-peak of the component specific to diabetes mellitus is peak A of FIG. 5 (the retention time is 3.7 min.). And the peak was detected in all of the 50 diabetic cases, while no such peak was detected in any of the 30 non-diabetic cases.

Figure 7:
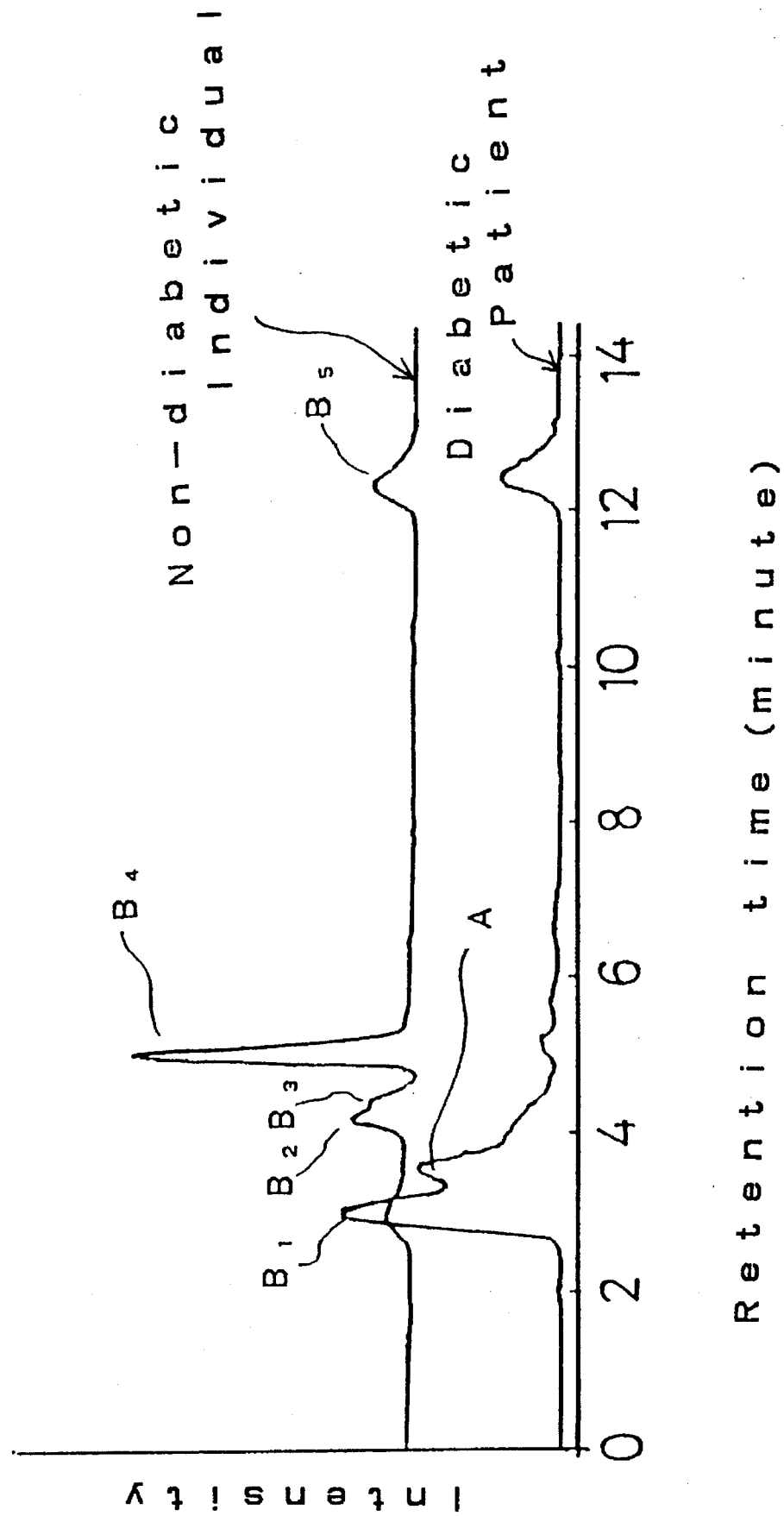
FIG. 7 is an explanatory view depicting the chromatogram from the analysis of the saliva samples from the diabetic patient and the non-diabetic individual in Example.

Furthermore, the individual chromatograms from a diabetic patient and a non-diabetic individual were recorded together in FIG. 7. Even in the figure, the diabetes mellitus specific-peak A having the 3.7 min. retention time also appears on the chromatogram of the diabetic patient, but no such peak appears on the chromatogram of the non-diabetic patient. Other peaks, B1, B2, B3, B4 and B5 appear in the-chromatograms of diabetic and non-diabetic patients.

Thus, the component specific to diabetic patients, which does not appear in non-diabetic patients, can be separated well with-the use of the zwitterionic stationary phase. Then, the separated component can be detected as a chromato-peak on chromatograms, so that the presence or absence of the specific peak can establish the diagnosis of diabetes mellitus in such a simple and reliable manner. The present method is not under the influence of the intake of diet, with the results of better reliability on the diagnosis and more advantage to testing personnel.

Using CHAPSO, namely 3-[(3-cholamidepropyl)dimethyl ammonio[-2-hydroxy-1-propanesulfonate (manufactured by Dojin Corporation) instead of the above CHAPS, the same test was done with the same results. When NaTDC, namely sodium taurodeoxycholate (manufactured by Sigma Corporation, USA) or NaTC, namely sodium taurocholate (manufactured by Sigma Corporation, USA) was used in the same manner, alternatively, the component specific to diabetes mellitus was not separated well.

In accordance with the present invention, various modification may be possible depending on the objective and the use within the scope of the present invention, without limitation to the specific example described above. That is, the chromatogram was used visually in the above example for diagnosis, without limitation. For example, the presence of the chromato-peak of the component specific to diabetes mellitus may be read mechanically (automatically) for diagnosis. In such case, the outcome of the diagnosis may be represented with a lamp or the like.

What is claimed is:

1. A method for aiding in the diagnosis of diabetes mellitus comprising injecting a saliva sample from a patient suspected of having diabetes mellitus into a stationary phase in a separation column, thereafter eluting a phosphate buffer as an eluent to separate analytes contained in the saliva sample, subsequently detecting the individual separated analytes with a UV detector and producing a chromatogram, and then identifying the presence or absence of a chromato-peak A of FIG. 5, said chromato-peak A representing a diabetes mellitus-specific component, wherein said stationary phase is a zwitterionic stationary phase comprising a support carrier and a zwitterionic charged layer selected from 3-[(3-cholamidepropyl)dimethyl ammonio]-1-propanesulfonate and 3-[(3-cholamidepropyl)dimethyl ammonio]-2-hydroxy-1-propanesulfonate.

* * * * *